United States Patent [19]

Okamoto et al.

[11] Patent Number: 5,919,670
[45] Date of Patent: Jul. 6, 1999

[54] PROCESS FOR PRODUCING L-AMINO ACIDS BY FERMENTATION

[75] Inventors: Kazuyuki Okamoto; Masato Ikeda; Kuniki Kino, all of Hofu, Japan

[73] Assignee: Kyowa Hakko Kogyo Co., Ltd., Tokyo, Japan

[21] Appl. No.: 09/099,036

[22] Filed: Jun. 18, 1998

[30] Foreign Application Priority Data

Jun. 23, 1997 [JP] Japan ................................. 9-165716

[51] Int. Cl.$^6$ ............................ C12P 13/04; C12P 13/08
[52] U.S. Cl. ...................... 435/106; 435/107; 435/108; 435/109; 435/110; 435/113; 435/114; 435/115; 435/116; 435/252.33; 435/252.8; 435/849
[58] Field of Search ................................ 435/106, 115, 435/252.33, 252.8, 849, 109, 107, 108, 110, 113, 114, 116

[56] References Cited

U.S. PATENT DOCUMENTS

| | | | |
|---|---|---|---|
| 4,463,094 | 7/1984 | Chibata et al. | 435/115 |
| 4,996,147 | 2/1991 | Furukawa et al. | 435/115 |
| 5,017,483 | 5/1991 | Furukawa et al. | 435/115 |
| 5,264,353 | 11/1993 | Yamada et al. | 435/115 |

FOREIGN PATENT DOCUMENTS

| | | |
|---|---|---|
| 50-31093 | 3/1975 | Japan . |
| 52-48195 | 4/1977 | Japan . |
| 56-10037 | 2/1981 | Japan . |
| 56-134993 | 10/1981 | Japan . |
| 58-893 | 1/1983 | Japan . |
| 60-12995 | 1/1985 | Japan . |
| 60-30693 | 2/1985 | Japan . |
| 61-195695 | 8/1986 | Japan . |
| 62-44193 | 2/1987 | Japan . |
| 63-273487 | 11/1988 | Japan . |
| 2-458 | 1/1990 | Japan . |
| 2-42988 | 2/1990 | Japan . |
| 4-330275 | 11/1992 | Japan . |

*Primary Examiner*—Herbert J. Lilling
*Attorney, Agent, or Firm*—Fitzpatrick, Cella, Harper & Scinto

[57] ABSTRACT

The present invention provides a process for producing an L-amino acid which comprises culturing in a nutrient medium a microorganism which is capable of producing the L-amino acid and which can not grow in a synthetic medium containing said L-amino acid as the sole nitrogen source in an amount of 5 mg/ml or below, allowing the L-amino acid to accumulate in the culture, and recovering the L-amino acid from the culture.

3 Claims, No Drawings

PROCESS FOR PRODUCING L-AMINO ACIDS BY FERMENTATION

BACKGROUND OF THE INVENTION

The present invention relates to a process for producing L-amino acids by fermentation. L-amino acids are used as drugs, food products and feed additives.

As the direct fermentation methods for producing L-amino acids directly from sugars, there are known methods in which mutants derived from wild type strains of microorganisms belonging to the genus Corynebacterium, Brevibacterium, Escherichia, Serratia or Arthrobacter are employed. For example, the following are known as L-amino acid-producing mutants: auxotrophic mutants which require amino acids, etc. (Japanese Published Examined Patent Application No. 10037/81), mutants which have resistance to amino acid analogues, vitamins, etc. (Japanese Published Unexamined Patent Application No. 134993/81, Japanese Published Unexamined Patent Application No. 44193/87), mutants which have both auxotrophic mutation and resistance mutation to amino acid analogues (Japanese Published Unexamined Patent Application No. 31093/75, Japanese Published Unexamined Patent Application No.134993/81), mutants which have lowered degradability (Japanese Published Unexamined Patent Application No. 273487/88, Japanese Published Examined Patent Application No. 48195/77) and mutants whose aminoacyl t-RNA-synthesizing enzymes have a decreased substrate affinity (Japanese Published Unexamined Patent Application No. 330275/92). Also known are transformants obtained by transformation with recombinant DNAs containing genes related to the biosynthesis of amino acids (Japanese Published Unexamined Patent Application No. 893/83, Japanese Published Unexamined Patent Application No. 12995/85, Japanese Published Unexamined Patent Application No. 30693/85, Japanese Published Unexamined Patent Application No.195695/86, Japanese Published Unexamined Patent Application No. 458/90, Japanese Published Unexamined Patent Application No. 42988/90).

Because of a growing demand for L-amino acids for use as drugs, food products and feed additives in recent years, there is an increasing need for the improvement of processes for producing L-amino acids. An object of the present invention is to provide an industrially efficient process for producing L-amino acids which are useful as drugs, food products and feed additives.

SUMMARY OF THE INVENTION

The present invention provides a microorganism which is capable of producing an L-amino acid and which can not grow in a synthetic medium containing said L-amino acid as the sole nitrogen source at a concentration of 5 mg/ml or below; and a process for producing an L-amino acid which comprises culturing said microorganism in a nutrient medium, allowing the L-amino acid to accumulate in the culture, and recovering the L-amino acid from the culture.

Examples of the L-amino acids produced in the present invention include L-asparagine, L-aspartic acid, L-alanine, L-arginine, L-isoleucine, L-glycine, L-glutamine, L-glutamic acid, L-cysteine, L-serine, L-tyrosine, L-tryptophan, L-threonine, L-valine, L-histidine, L-phenylalanine, L-proline, L-methionine, L-lysine, L-leucine, etc. A preferabe example is L-threonine.

DETAILED DESCRIPTION OF THE INVENTION

Generally, microorganisms have enzymes having the activity to release ammonia from L-amino acids, such as L-amino acid dehydrogenase, L-amino acid oxidase and L-amino acid dehydratase, and enzymes having the activity to transfer ammonia from L-amino acids to keto acids, such as L-amino acid transaminase, and thus can grow in a synthetic medium containing an L-amino acid as the sole nitrogen source at such a low concentration as 5 mg/ml or below.

In accordance with the present invention, L-amino acid productivity can be improved by the use of a microorganism which is capable of producing the L-amino acid and which can not grow in a synthetic medium containing said L-amino acid as the sole nitrogen source in an amount of 5 mg/ml or below, whereby an industrially efficient process for producing L-amino acids is provided.

In the present invention, any microorganism may be used so long as it is capable of producing an L-amino acid and can not grow in a synthetic medium containing said L-amino acid as the sole nitrogen source at a concentration of 5 mg/ml or below. For example, microorganisms belonging to the genus Corynebacterium, Brevibacterium, Escherichia, Serratia or Arthrobacter which are capable of producing an L-amino acid and can not grow in a synthetic medium containing said L-amino acid as the sole nitrogen source at a concentration of 5 mg/ml or below may be used. Examples of the suitable species include *Corynebacterium glutamicum, Brevibacterium ammmoniagenes, Escherichia coli, Serratia marcescens* and *Arthrobacter paraffineus*. A typical example of a suitable strain is *Escherichia coli* H-9244 THN-1 strain.

The microorganisms of the present invention can be obtained by subjecting microorganisms capable of producing an L-amino acid to a conventional mutation treatment, or cell fusion, transduction or other recombinant DNA techniques, and then by selecting microorganisms which can not grow in a synthetic medium containing the L-amino acid as the sole nitrogen source in an amount of 5 mg/ml or below.

The microorganisms of the present invention may additionally have properties to improve L-amino acid productivity, for example, auxotrophic mutation, drug resistance and drug sensitivity.

As the synthetic medium, a minimal medium can be employed when the microorganism of the present invention is aprototroph. When the microorganism of the present invention is an auxotroph, a medium prepared by adding the required nutrient to the minimal medium can be employed.

The production of L-amino acids by using the microorganisms of the present invention can be carried out by an ordinary method for culturing bacteria.

As the medium used for the production of L-amino acids, any of synthetic media and natural media can be employed as long as it appropriately contains carbon sources, nitrogen sources, inorganic substances and trace amounts of nutrients which the strain used requires.

Examples of the carbon sources include carbohydrates such as glucose, fructose, lactose, molasses, cellulose hydrolyzate, crude sugar hydrolyzate and starch hydrolyzate, organic acids such as pyruvic acid, acetic acid, fumaric acid, malic acid and lactic acid, and alcohols such as glycerin and ethanol.

Examples of the nitrogen sources include ammonia, various inorganic salts (such as ammonium chloride, ammonium sulfate, ammonium acetate and ammonium phosphate), ammonium salts of organic acids, amines, peptone, meat extract, corn steep liquor, casein hydrolyzate, soybean cake hydrolyzate, various fermented cells and digested matters thereof.

Examples of the inorganic substances include potassium dihydrogenphosphate, dipotassium hydrogenphosphate, magnesium phosphate, magnesium sulfate, magnesium chloride, sodium chloride, ferrous sulfate, manganese sulfate, copper sulfate, calcium chloride and calcium carbonate.

Culturing is carried out under aerobic conditions, for example, by shaking culture or spinner culture under aeration. The culturing temperature is in the range of 20 to 40° C., preferably 28 to 37° C. The pH of the medium is in the range of pH 5 to 9, preferably around neutrality. The pH adjustment is carried out by using calcium carbonate, an organic or inorganic acid, an alkali solution, ammonia, a pH buffer, etc. Usually, an L-amino acid is formed and accumulated in the culture by 1 to 7 days of culturing.

After the culturing is completed, precipitates such as cells are removed from the culture, and the L-amino acid can be recovered from the culture by means of ion exchange chromatography, concentration, salting-out, etc. in combination.

Certain embodiments of the invention are illustrated in the following Examples.

EXAMPLE 1

Acquisition of microorganisms which can not grow in a synthetic medium containing an L-amino acid as the sole nitrogen source in an amount of 5 mg/ml or below

*Escherichia coli* H-7700, which is a non-diaminopimelic-acid-requiring strain derived from *Escherichia coli* H-4581 (FERMBP-1411) having requirement for diaminopimelic acid, was subjected to mutation treatment using N-methyl-N'-nitro-N-nitrosoguanidine according to a conventional method (0.2 mg/ml, at 30° C. for 30 minutes), and then spread on a synthetic agar plate medium [0.5% glucose, 0.3% potassium dihydrogenphosphate, 0.6% disodium hydrogenphosphate, 0.01% magnesium sulfate, 0.2% ammonium chloride, 20 mg/l calcium chloride, 20 mg/l required nutrient (DL-methionine) and 2% agar, pH 7.2].

Culturing was carried out at 30° C. for 2 to 6 days, and the colonies growing on the plate (about $10^4$) were picked up and replicated on synthetic agar media containing L-threonine as the sole nitrogen source in place of ammonium chloride in the above synthetic medium at a concentration of 1 mg/ml and 10 mg/ml, respectively.

Culturing was carried out at 30° C. for 2 days, and about 30 strains were obtained which could not grow on the medium containing 1 mg/ml L-threonine but could grow on the medium containing 10 mg/ml L-threonine.

L-threonine production test was carried out on the obtained strains in the same manner as in Example 3.

A strain having markedly improved L-threonine productivity was named *Escherichia coli* H-9244 THN-1.

The strain H-9244 THN-1 was deposited with the National Institute of Bioscience and Human-Technology, Agency of Industrial Science and Technology on Jun. 19, 1997 as FERM BP-5985 under the Budapest Treaty.

EXAMPLE 2

Comparative test on the growth of the strains on synthetic agar plate media containing L-threonine as the sole nitrogen source The degree of growth of the mutant H-9244 THN-1 obtained in Example 1 was compared with that of the parent strain H-7700 using synthetic agar plate media containing L-threonine as the sole nitrogen source.

Each of the strains which had been cultured in a natural medium for 24 hours was suspended in physiological saline, and the resulting suspension was spread on synthetic agar plate media containing L-threonine as the nitrogen source at varied concentrations (1 to 15 mg/ml) and 20 mg/l DL-methionine which is the required amino acid at a cell density of 1 to 10 cells/cm². Culturing was carried out at 33° C. for 4 days.

The sizes of the colonies which appeared on the media by the culturing are shown in Table 1.

H-7700 strain could grow on any of the synthetic agar media containing L-threonine as the sole nitrogen source, whereas H-9244 THN-1 strain could not grow at all on the synthetic agar media containing L-threonine as the sole nitrogen source at concentrations of 5 mg/ml or below.

TABLE 1

| Strain | Nitrogen source (L-threonine) | | | | | | | |
|---|---|---|---|---|---|---|---|---|
| | 0 | 1 | 3 | 5 | 7 | 10 | 15 | (mg/ml) |
| H-7700 | − | ± | + | + | + | + | + | |
| H-9244 THN-1 | − | − | − | − | ± | ± | + | |

+: Good growth (colony size: 1–3 mm)
±: Capable of growth (colony size: ≦0.5 mm)
−: No growth (No colony formation observed)

EXAMPLE 3

Production of L-threonine

Production of L-threonine using the mutant H-9244 THN-1 obtained in Example 1 and its parent strain H-7700 was carried out in the following manner.

Each of H-9244 THN-1 strain and H-7700 strain was inoculated into 6 ml of a seed medium (2% glucose, 1% peptone, 1% yeast extract, 0.25% NaCl, 130 mg/l DL-methionine and 1% calcium carbonate, pH 7.0) in a large test tube, followed by shaking culture at 30° C. for 16 hours.

Then, 0.1 ml of the obtained seed culture was inoculated into 5 ml of a production medium (6% glucose, 0.2% corn steep liqour, 1.6% ammonium sulfate, 0.1% potassium dihydrogenphosphate, 100 mg/l DL-methionine, 4% magnesium phosphate and 1% calcium carbonate, pH 7.0) in a large test tube, followed by shaking culture at 30° C. for 48 hours.

After the culturing was completed, the amount of L-threonine accumulated in the culture was determined by high performance liquid chromatography.

The results are shown in Table 2.

The L-threonine productivity of H-9244 THN-1 strain was significantly improved compared with that of the parent strain H-7700.

TABLE 2

| Strain | L-threonine (g/l) |
|---|---|
| H-7700 | 1.5 |
| H-9244 THN-1 | 5.0 |

What is claimed is:

1. A process for producing an L-amino acid which comprises culturing in a nutrient medium a microorganism belonging to the species *Escherichia coli* which is capable of producing said L-amino acid and which cannot grow in a synthetic medium containing said L-amino acid as sole nitrogen source in an amount of 5 mg/ml or below, allowing the L-amino acid to accumulate in the culture, and recovering the L-amino acid from the culture.

2. The process according to claim 1, wherein said microorganism is *Escherichia coli* H-9244 THN-1.

3. The process according to either of claim 1 or 2, wherein said L-amino acid is L-threonine.

* * * * *

UNITED STATES PATENT AND TRADEMARK OFFICE
CERTIFICATE OF CORRECTION

PATENT NO. : 5,919,670

DATED : July 6, 1999

INVENTOR(S) : KAZUYUKI OKAMOTO ET AL.

It is certified that error appears in the above-identified patent and that said Letters Patent is hereby corrected as shown below:

COLUMN 1

Line 61, "preferabe" should read --preferable--.

COLUMN 2

Line 25, "ammmoniagenes," should read --ammoniagenes,--; and
Line 42, "aprototroph." should read --a prototroph.--.

COLUMN 3

Line 26, "(FERMBP-1411)" should read --(FERM BP-1411)--.

UNITED STATES PATENT AND TRADEMARK OFFICE
CERTIFICATE OF CORRECTION

PATENT NO. : 5,919,670

DATED : July 6, 1999

INVENTOR(S) : KAZUYUKI OKAMOTO ET AL.

It is certified that error appears in the above-identified patent and that said Letters Patent is hereby corrected as shown below:

COLUMN 4

Line 32, "liqour," should read --liquor,--; and
Line 64, "claim 1" should read --claims 1--.

Signed and Sealed this

Seventh Day of March, 2000

Attest:

Attesting Officer

Q. TODD DICKINSON

Commissioner of Patents and Trademarks